United States Patent
Furr et al.

(12)

(10) Patent No.: US 6,364,866 B1
(45) Date of Patent: Apr. 2, 2002

(54) SYRINGE LOADING AID

(76) Inventors: Douglas Furr, 1228 E. Teton Dr., Lindon, UT (US) 84042; Ian M. Dawe, 962 W. 530 North, Pleasant View, UT (US) 84062; Andrew J. Dawe, 1108 N. 700 East, Mapleton, UT (US) 84664

( * ) Notice: Subject to any disclaimer, the term of this patent is extended or adjusted under 35 U.S.C. 154(b) by 0 days.

(21) Appl. No.: 09/235,537

(22) Filed: Jan. 22, 1999

(51) Int. Cl.$^7$ ............................................. A61B 19/00
(52) U.S. Cl. ...................... 604/414; 141/330; 141/375
(58) Field of Search ................................ 604/411, 413, 604/414, 187, 403, 207, 208; 141/18, 21, 25–28, 94, 97, 329, 330, 375, 383

(56) References Cited

U.S. PATENT DOCUMENTS

| | | | |
|---|---|---|---|
| 3,833,030 A | * 9/1974 | Waldbauer, Jr. et al. ...... 141/26 |
| 3,844,318 A | 10/1974 | Raia et al. | |
| 3,853,158 A | 12/1974 | Whitty | |
| 4,219,055 A | 8/1980 | Wright | |
| 4,357,971 A | 11/1982 | Friedman | |
| 4,475,915 A | 10/1984 | Sloane | |
| 4,883,101 A | 11/1989 | Strong | |
| 4,998,570 A | 3/1991 | Strong | |
| 5,247,972 A | 9/1993 | Tetreault | |
| 5,292,318 A | 3/1994 | Haber et al. | |
| 5,356,406 A | * 10/1994 | Schraga ...................... 604/415 |
| 5,377,725 A | 1/1995 | Neff | |
| 5,385,559 A | 1/1995 | Mannix | |
| 5,468,233 A | 11/1995 | Schraga | |
| 5,487,738 A | 1/1996 | Sciulli | |
| 5,498,243 A | * 3/1996 | Vallelunga et al. | |
| 5,697,916 A | 12/1997 | Schraga | |
| 5,746,714 A | * 5/1998 | Salo et al. ..................... 604/68 |
| 5,873,859 A | * 2/1999 | Muntz ......................... 604/207 |

* cited by examiner

Primary Examiner—Richard K. Seidel
Assistant Examiner—Jeremy Thissell
(74) Attorney, Agent, or Firm—Kirton & McConkie

(57) ABSTRACT

A syringe loading device is disclosed that includes a vial holder, a syringe insertion guide and holder, a transparent cover mounted to the vial holder and syringe insertion guide and holder, and an ejection button. The vial holder is adapted to hold a vial containing liquid contents and has an integrated interference snap fit to removably receive a cap of the vial. The syringe insertion guide and holder, which is placed adjacent the vial holder and integrated therewith, is adapted to allow a syringe having a needle at one end to be removably inserted, needle end first, into the syringe insertion guide and holder with the needle penetrating into the vial. The syringe insertion guide and holder also has biased syringe clamps that hold the body of the syringe in a removably fixed position. The transparent cover slidably mounts parallel to the vial holder and syringe insertion guide and holder to protect the vial and syringe when placed in the syringe holder. The transparent cover slides to a first position uncovering the vial holder and to a second position to cover the holder. In the uncovered position, the syringe can be inserted into the insertion guide and holder. The cover can be placed in an intermediate position to allow ejection of the syringe for removal. The push button vial ejector fits within the vial holder and adjacent to interference snap fit.

13 Claims, 5 Drawing Sheets

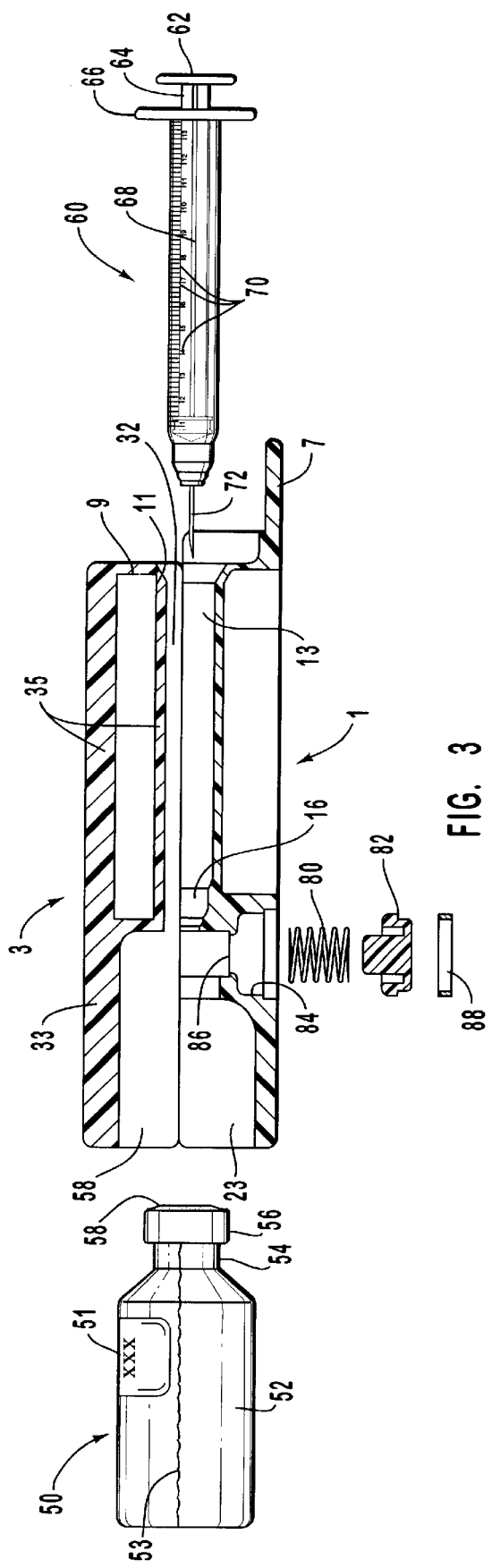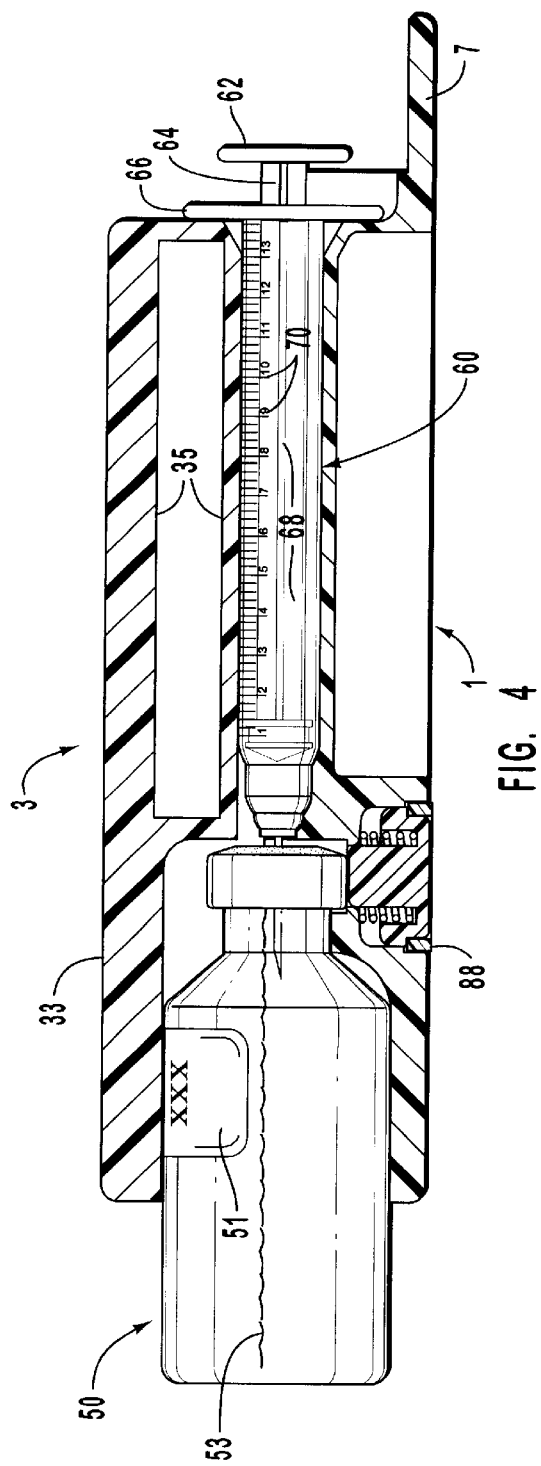

SYRINGE LOADING AID

BACKGROUND OF THE INVENTION

1. The Field of the Invention

The present invention relates generally to the field of devices for facilitating the use of hypodermic syringes. More particularly, the present invent ion is an apparatus for improving the safety, efficiency and accuracy of loading hypodermic syringes from medicine vials.

2. The Relevant Technology

Devices designed to facilitate the loading of hypodermic syringes are common in the art. These devices range from very simple alignment devices to complicated electro-mechanical devices with levers, gearing and digital electronics. Many of these devices are designed for users who are sight-impared or who are physically impaired in some way which renders manipulation of small objects difficult.

The prior art contains many devices which help measure the amount of liquid entering the syringe. These include devices with audible signals that identify fixed amounts of liquid as they are loaded into the syringe. This is done through mechanical clicking devices as well as electrical and electronic beepers or synthesized voice. The object of this feature is to allow the sight-impaired user to load the correct dosage by audible indications independent of sight, however prior art devices which measure dosage with audible signals are typically complicated, and expensive.

Most syringes have graduated markings on the barrel section which indicate the volume of liquid held within the syringe. These markings are typically quite small and can be difficult to read—especially to the sight-impaired. Medicine vials also have labels printed in small text which identify the vial contents. Many patients, such as diabetics, may need injections with different formulations during a given time period. In this situation, vial identification becomes as critical as measuring the correct dosage quantity. What is needed is a device which will magnify the syringe markings and the vial label in order to make them more readable thereby facilitating the process of drawing a correct dosage of the proper medicine.

In order to extract a dosage of medicine, the syringe user must typically insert the syringe needle into a flexible self-sealing plug in the lid of a standard medicine vial. This plug, usually made of rubber or similar material is known as a septum. The septum is usually quite small and users often have difficulty inserting a needle into its small area. Missing the septum can result in contamination of the needle and injury to the user.

What is needed is a device that is specifically designed for the physically impaired user who may have poor or limited motor skills and decreased strength in the hands and fingers. The device must be ergonomically designed so that a physically impaired user can use the device without undue stress and pain. Furthermore, the device must be safe for the physically impaired user. This can be achieved through the use of a needle guide that completely surrounds the area into which the syringe is placed for loading.

Physically impaired users may also benefit from a device that can be mounted on a table or wall or other convenient location. This allows the user to manipulate the device without worrying about supporting or holding it.

Also needed is protection for fragile medicine vials while they are stored in the device. These vials can be easily broken and the cap and septum portion can be easily damaged from impact while handling. A device that holds the vial snugly and surrounds the vial protecting it from impact is necessary for patient users who may need injections on-the-go or for professionals in a busy workplace as this allows the user to leave the vial in the loading aid between uses. Simplicity and portability are also important in a syringe loading aid.

Vials are easily damaged when the cap is wedged in a device but they must be held firmly to protect them during use. The solution to this problem is a snug fitting device with a specially designed ejection mechanism that properly ejects the vial from the device without twisting, prying or other undue force.

Devices that fit only one or few syringe sizes have limited utility. A device that services numerous standard syringe sizes is necessary for the professional user or the patient who must inject multiple medicines or dosages.

SUMMARY AND OBJECTS OF THE INVENTION

Accordingly, it is an object of the present invention to provide a syringe loading aid that is ergonomically designed for the physically impaired. The present invention has an hour-glass-like shape that narrows in the center and at the ends to provide an easy grip. Additionally, the edges of the present invention are knurled to eliminate slippage. This shape and surface treatment provide a sure grip for users even when motor skills and strength are compromised. Also, the present invention may be used in a number of positions as held in the hand, placed on an inclined or flat surface or mounted on a wall. This feature makes it more easily usable to the physically impaired as they do not have to concentrate on the orientation of the device while trying to extract a dosage.

A further object of the present invention is the prevention of injury from needle stabs and the preservation of a functional sterile needle. This is achieved with a 360 degree needle guide that serves to direct the syringe needle into a syringe compartment, prevent needle damage and user injury. The needle guide of the present invention completely surrounds the entrance to the syringe compartment so that a near miss in any direction will be guided back into the compartment. The hour-glass shape of the present invention also provides a hand grip at a safe distance from the needle guide entrance making finger injuries less likely.

Furthermore, the present invention includes a safety tab rising adjacent to the entrance to the syringe compartment which serves to prevent an errant needle from passing behind the device and into the user's hand. Not only the user, but the needle is threatened by a missed attempt at the syringe compartment. Needles may be bent, dulled or broken and their sterility may be compromised when a user misses the proper target.

An additional object of the present invention is protection of the vial while it is stored in the device. The present invention surrounds the vial's sides, neck and cap with a resilient plastic material, typically acrylic. This protects the vial from many impacts and allows the device to be placed in almost any position such as in a pocket or briefcase without threatening the vial's structural integrity or the sterility of the septum. In addition to surrounding portions of the vial, the present invention positively locks around the neck and the cap of the vial with a snap fit that snugly holds the vial in place so that is does not vibrate or rattle within the device. This further protects the vial from damage.

Because vials are quite fragile they can be difficult to remove from a snug fit. Twisting and prying can damage the cap, break the vial or compromise the seal. The present invention utilizes a push button release mechanism located directly adjacent to the location of the vial cap when it is snapped into the device. This mechanism allows for easy ejection of the vial from the device without damaging the vial. This allows for multiple insertion and ejection of a vial during its lifetime, enables the user to mix medicines from different vials in one syringe dosage and provides a way to remove a vial so it can be stored elsewhere while the device is used for another patient or injection type.

An additional object of the present invention is the ability to function with several syringe sizes. While syringes have evolved into standard size formats, several standard sizes remain due to the need for different dosage quantities. A professional and even a patient-user may be required to use syringes of different size during a given time period. Using multiple syringe loading aids would be uneconomical. Therefore, the present invention uses a novel friction-creating clenching mechanism, described in detail in the description of the preferred embodiment below, to firmly hold syringes of differing length and diameter by resisting syringe movement both laterally and longitudinally.

Yet another object of the present invention is a novel syringe ejection mechanism which helps to release the syringe from the resistance of the clenching mechanism. This feature allows the syringe to be tightly held in the device while transporting or drawing a dosage, yet easily ejected when an injection is desired. Syringe ejection is accomplished by sliding the magnification lens component toward the plunger end of the syringe thereby contacting the hilt or finger tabs of the syringe and sliding the syringe out of the device. The physically impaired will find the size and shape of the magnifying lens component much easier to manipulate than the small hilt of the syringe and will more easily eject a syringe than if direct manipulation of the syringe hilt were required.

Another significant objective of the present invention is to provide a syringe loading aid that can be permanently or detachably mounted to a wall, table, cabinet or other surface thereby allowing the user to operate the device without actively holding or orienting the device. This may allow the user to operate the device with one hand, further accommodating the physically impaired, or it may allow the user to use both hands to draw a dosage into the syringe without worrying about holding a vial or orienting the device. To effectuate this end the present invention includes mounting structures which can be formed with holes, tabs or other formations to allow attachment to other objects. Screws or other typical fasteners may be employed to attach the present invention to another object.

BRIEF DESCRIPTION OF THE DRAWINGS

In order that the manner in which the above-recited and other advantages and objects of the invention are obtained, a more particular description of the invention briefly depicted above will be rendered by reference to a specific embodiment thereof which is illustrated in the appended drawings. With the understanding that these drawings depict only a typical embodiment of the invention and are not therefore to be considered to be limiting of its scope, the invention will be described and explained with additional specificity and detail through the use of the accompanying drawings in which:

FIG. 3 is a longitudinal section of the present invention showing a syringe as it would enter the device, a vial detached from the device and the vial ejection mechanism in an exploded sectional view.

FIG. 4 shows the present invention in longitudinal section with the vial properly inserted into the invention, a syringe fully inserted into the invention and the cover section of the invention in proper position for filling the syringe.

DETAILED DESCRIPTION OF THE PREFERRED EMBODIMENT

The figures listed above are expressly incorporated as part of this detailed description.

It will be readily understood that the components of the present invention, as generally described and illustrated in the figures herein, could be arranged and designed in a wide variety of different configurations. Thus, the following more detailed description of the embodiments of the system and method of the present invention, as represented in FIGS. 1 through 8, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

The preferred embodiment of the present invention is comprised of a base 1 and a cover 3 which is slidably and removably attached to the base 1 along an L-shaped track 25 formed into the base. The cover 3 has an L-shaped runner or flange 27 which engages the track 25 allowing the cover 3 to slide longitudinally along the base 1 while restraining lateral movement.

Figure 1:
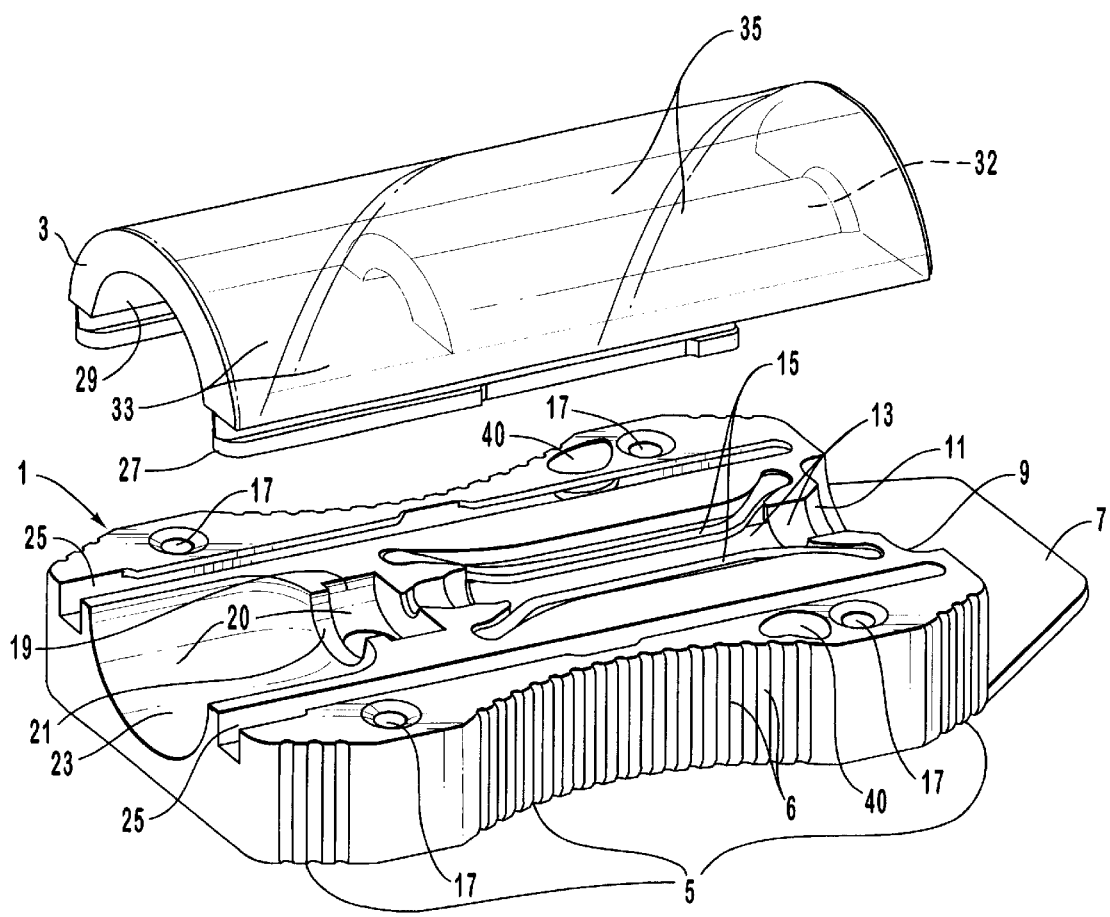
FIG. 1 is a perspective view of the present invention showing the cover section detached from the base section.
Figure 2:
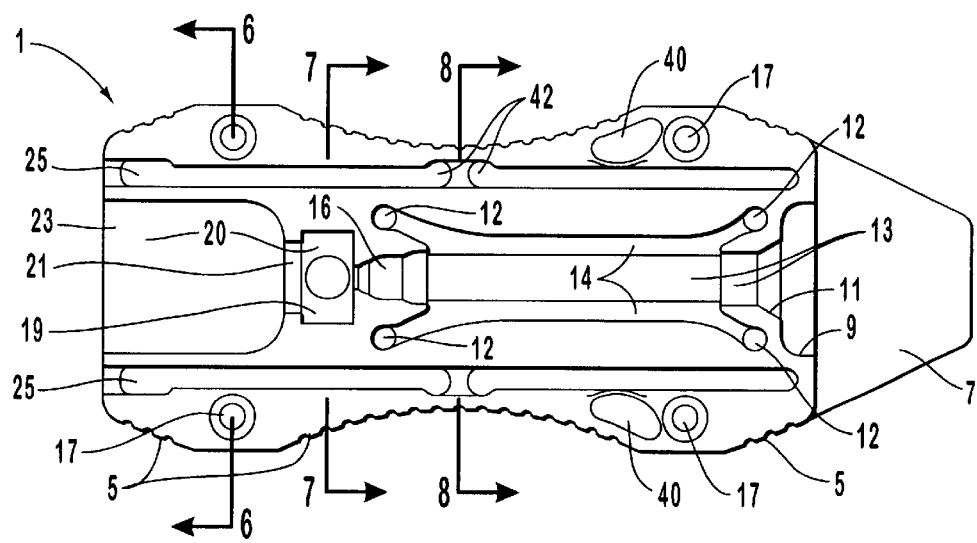
FIG. 2 is a top plan view of the base section of the present invention.
Figure 5:
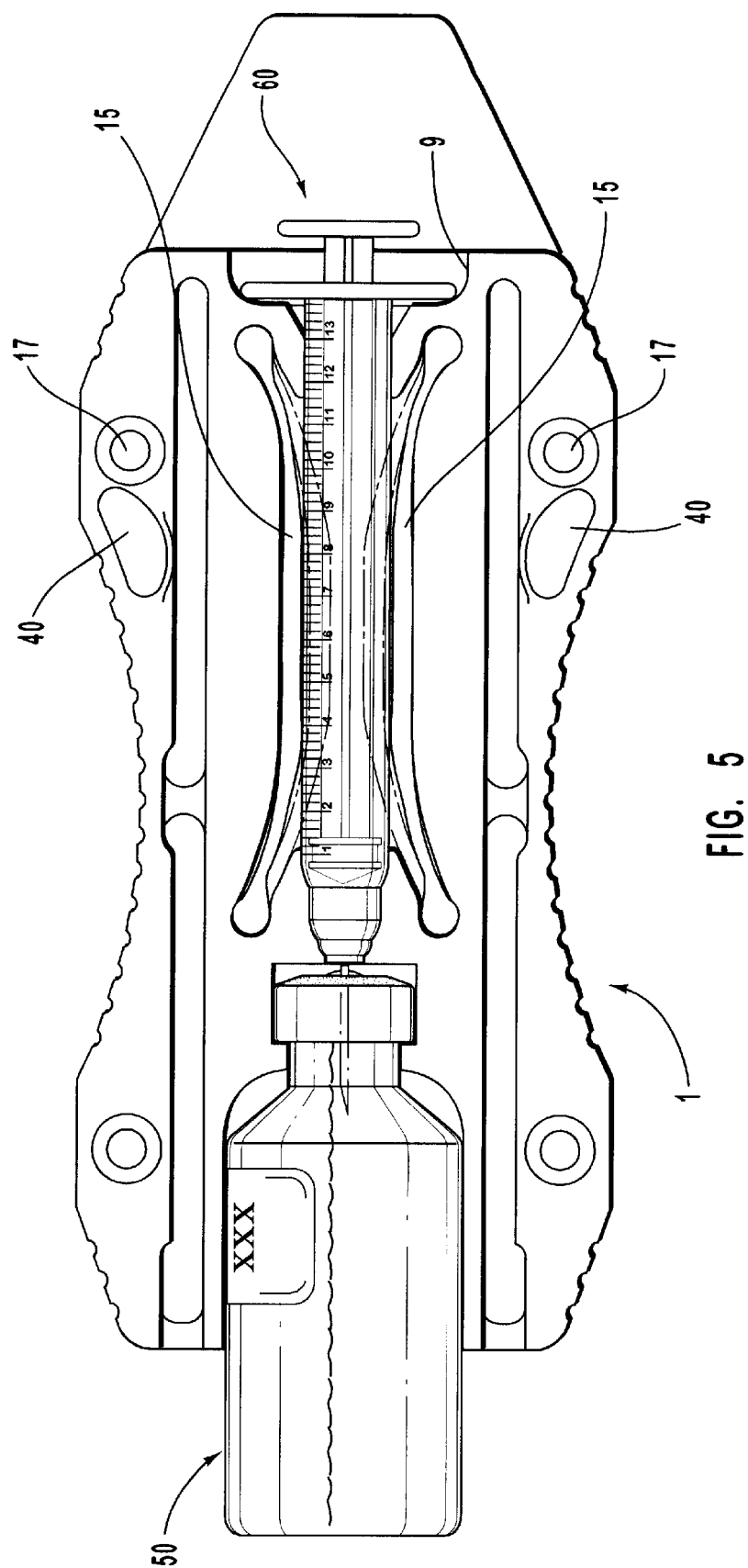
FIG. 5 displays a top view of the present invention with a vial inserted therein and a syringe fully inserted into the invention. The cover is not shown for clarity.
Figure 6:
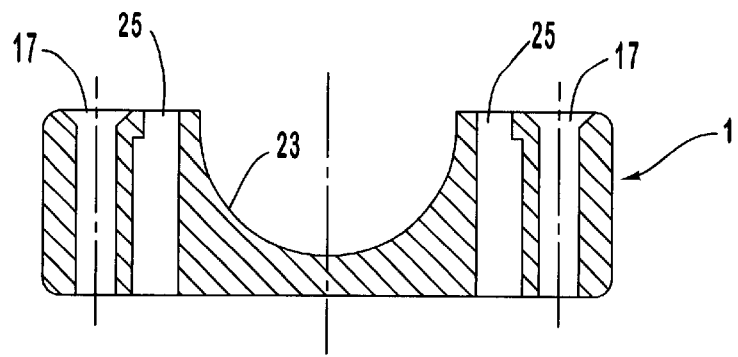
FIG. 6 is a transverse sectional view of the vial cavity looking out of the vial end of the present invention.

The base 1 has an ergonomically functional shape 5 which takes the rough form of an hour-glass. This shape 5 has a narrow cross-section near the middle of the invention which increases in width as it progresses toward the ends. After reaching a maximum width, the shape of the present invention then tapers to form ends which are narrower than its maximum width as shown in FIGS. 1, 2 and 5. To further enhance its ergonomic design, the present invention has a knurled surface 6 along the exterior sides which provides traction against slippage in the hands.

The base 1 contains a vial cavity 20 for securely holding a medicine vial therein. This vial cavity is further subdivided into a vial body section 23, a vial neck section 21 and a vial cap section 19. The vial body section 23 is shaped to closely, but loosely fit around the body of a medicine vial 52 so as to protect the vial from some impacts while avoiding undue pressure on the fragile vial body. Vial body section 23 may partially extend down the sides of vial 50 as shown in the accompanying illustrations of the preferred embodiment or it may completely extend past the base of vial 50 to fully protect the vial from impacts. The preferred embodiment does not extend to the base of the vial in order to allow vial manipulation for mixing and provide a more compact design.

Figure 7:
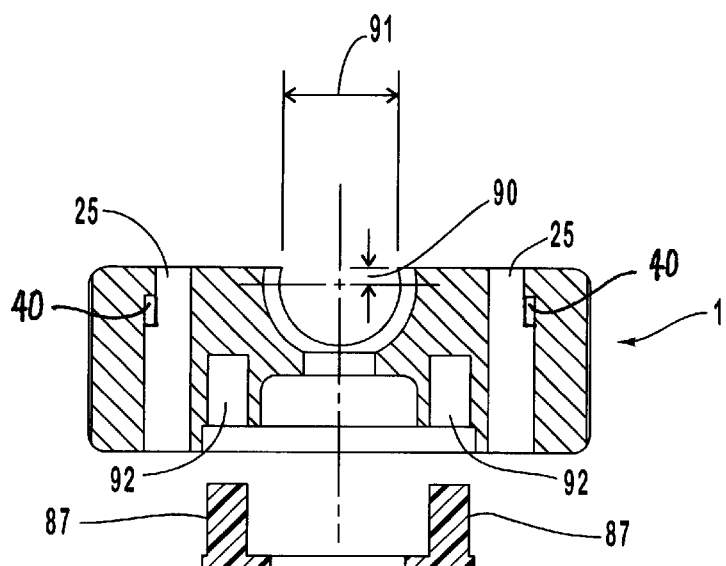
FIG. 7 is a transverse sectional view of the vial cavity where the vial cap snaps into the present invention.
Figure 8:
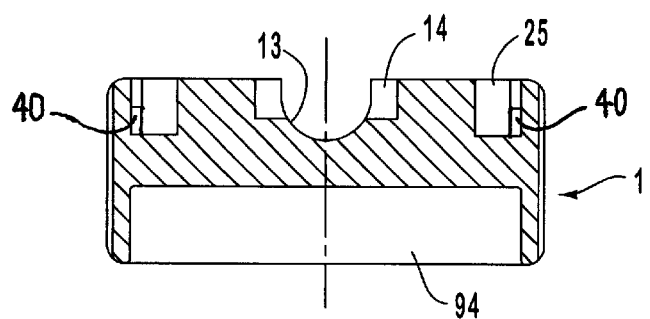
FIG. 8 is a transverse sectional view of the syringe cavity looking out the syringe end of the present invention.
Figure 9:
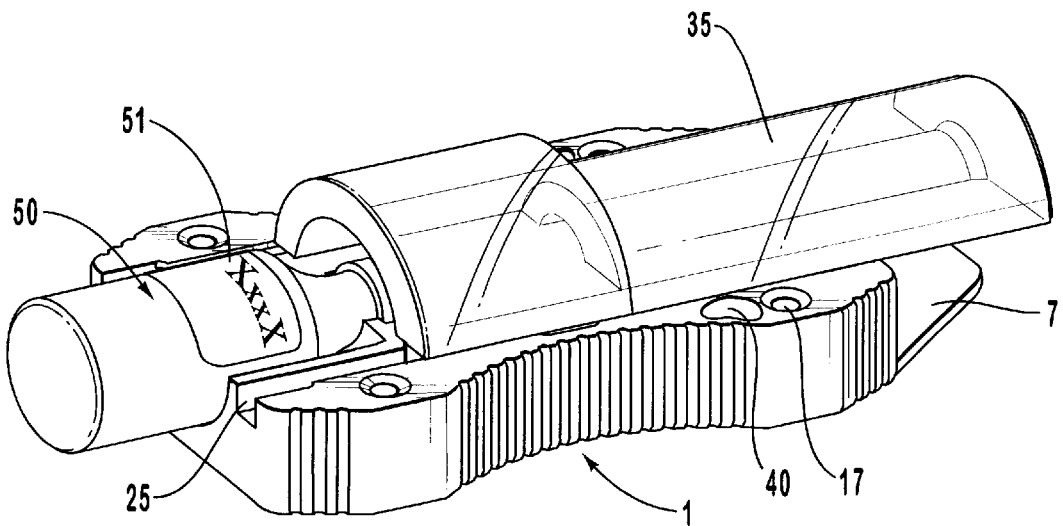
FIG. 9 is a perspective view of the present invention showing the cover section slid into a position where the vial may be accessed.
Figure 10:
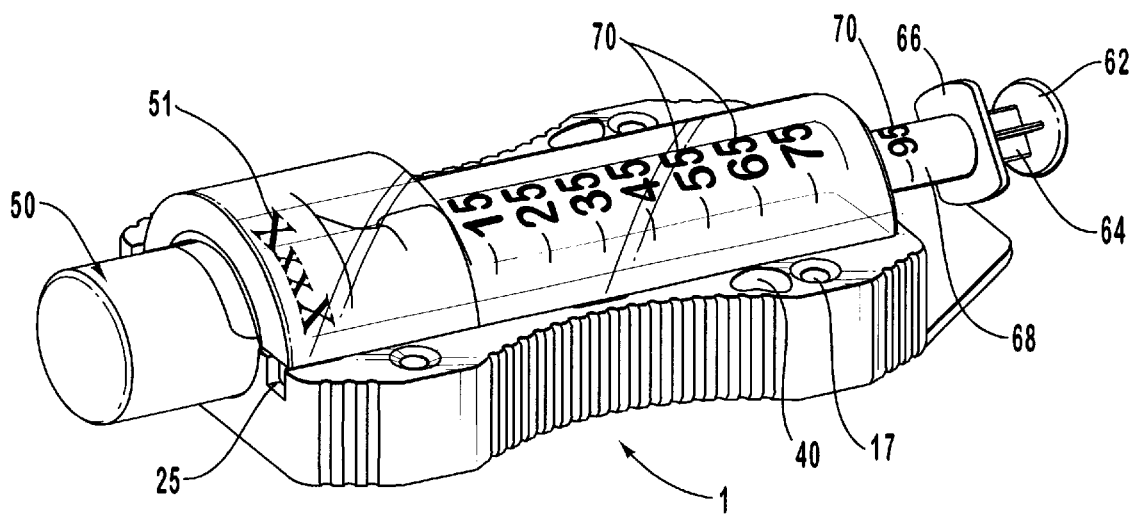
FIG. 10 is a perspective view of the present invention with the cover slid into the syringe loading position showing the magnification of the syringe markings and the vial label.

The vial neck section 21 of the vial cavity is shaped to form an interference snap fit around the neck of the medicine vial 54. The vial cap section 19 is also shaped to form an interference snap fit around the vial cap 56. This interference snap fit is specifically designed to firmly and snugly hold the vial 50 in the base 1 and prevent longitudinal and lateral movement of the vial 50 within the base 1. In the presently preferred embodiment of the present invention this interference snap fit is achieved using an interference fit in the vial neck section 21 and the vial cap section 19. To achieve this interference fit, the substantially semi-circular shape of the vial cavity at the vial neck section 21 and the vial cap section 19 extends beyond a half circle to lock the vial 50 into the base 1. This snap fit is shown in FIG. 7 where the vial neck section 21 of the vial cavity 23 continues beyond a half circle for 0.060 inches 90 thereby forming an interference fit at the mouth 91 of the vial cap section 19 and a similar fit for the vial neck section 21. While other dimensions may be successfully used for this fit, the dimension of 0.060 inches has been found to provide optimum holding characteristics while allowing easy release of the vial 50 from the base 1 via a vial release mechanism 80 to 88.

Also contained in base 1 is a vial release mechanism which is contained in a release mechanism cavity 84. The vial release mechanism is comprised of a vial release button 82, a button return spring 80, a button retainer 88, a release mechanism cavity 84 and a release mechanism contact port 86. The vial release button 82 and spring 80 are held within release mechanism cavity 84 by button retainer 88 shown in FIG. 7. Button retainer 88 may be attached to base 1 by pegs 87 which press fit or interference fit into peg holes 92 in base 1 or it may be attached to base 1 by screws, rivet, cement, adhesive or other conventional fasteners. The vial release mechanism is activated by pressing release button 82 thereby compressing spring 80 and forcing button 82 through contact port 86 and into contact with vial cap 56 thereby pushing vial cap 56 out of its interference snap fit in vial cap section 19 of the vial cavity and releasing vial 50 from base 1.

Base 1 also comprises a syringe cavity 13 for guiding a syringe and its needle into the medicine vial and helping to hold the syringe in position while a user draws a dosage into the syringe. Syringe cavity 13 connects to vial cap section 19 of the vial cavity 20 through syringe stop 16 which allows a syringe needle 72 to pass from syringe cavity 13 into a vial 50 contained in the vial cavity 20. Syringe cavity 13 is flanked on either side by clench recesses 14 into which clench tensioners 15 recede when a syringe is placed into syringe cavity 13 as shown in FIG. 5. These clench tensioners 15 are elongated elastic elements with pegs which extend in a substantially perpendicular direction from each end of the elongated elements. The tensioner pegs hold the tensioners in place when they are inserted into tensioner holes 12 formed in the base 1.

At the mouth or entrance to the syringe cavity is a tapered conical needle guide 11 which completely surrounds the entrance to the syringe cavity providing a continuous funnel shaped surface to guide a stray needle into the syringe cavity. A portion of needle guide 11 is formed into the base 1 while the remaining portion is formed into cover 3. A syringe hilt recess 9 surrounds the needle guide 11 providing a means for accommodating shorter syringes by allowing them to enter further into the syringe cavity 13 and into the vial 50.

The base 1 further comprises mounting elements 17 by which the present invention may be mounted to a wall, table, cabinet, mounting bracket or other fixture. These mounting elements may take the form of holes formed in the base through which screws, rivets, pegs or other standard fasteners may be placed, either temporarily or permanently, as shown in the preferred embodiment. The base 1 may also be mounted to a bracket or stand to hold the present invention in the proper position for loading a syringe.

Cover 3 of the present invention is slidably attachable to base 1 by inserting the cover flanges 27 into the base tracks 25. Cover 3 has a vial magnification lens 33 and a syringe magnification lens 35. Also contained in cover 3 are a vial containment area 29 and a syringe containment area 32.

During normal use, the flanges 27 are inserted into the tracks 25 and the cover 3 is slid toward the syringe cavity 13 end of the base 1. In this position, the cover 3 allows access to the vial cavity 20 so that a medicine vial may be placed into the vial cavity 20. At this point, the vial 50 is placed into the vial cavity 20 and oriented so that the label 51 will be visible through the vial magnification lens 33 when the cover 3 is slid over the vial 50. Once the vial 50 is placed in vial cavity 20 and pushed into a snap fit engagement, the cover 3 is slid back toward the vial cavity 20 so that the vial magnification lens 33 affords an improved view of the vial label 51 and the vial contents 53.

In this position, the syringe cavity end of the cover 3 aligns with the syringe cavity end of the base 1 forming a syringe needle guide 11 that completely surrounds the entrance to the syringe cavity 13. This syringe needle guide 11 directs the needle 72 into the syringe cavity 13 from near misses in all directions. Protector tab 7 also helps redirect wayward needles and protects the user from sharp needles that miss their target. With the cover 3 in this position a syringe 60 and accompanying needle 72 may be inserted into the syringe cavity 13 where they will be guided into proper alignment with the vial 50 so that the syringe 60 may be filled with the proper dosage of vial contents 53. Once the syringe 60 is fully inserted into the syringe cavity 13 and the needle 72 is guided into the vial 50 puncturing the septum 58, the user may observe the syringe markings 70 through the syringe magnification lens 35 which renders the syringe markings 70 more easily readable.

As the syringe 72 enters the syringe cavity 13, the syringe contacts tensioners 15 forcing the tensioners outward into tensioner recesses 14 thereby creating friction between the syringe 72 and the tensioners 15. This friction will typically hold the syringe 72 in the syringe cavity 13 while the plunger 62 is retracted to fill the syringe. However, if a syringe does not develop enough friction to remain in place during plunger retraction, the user may have to place a thumb or finger over the syringe hilt 66 while the plunger is being retracted.

Once the syringe 72 is filled and the proper dosage is verified through magnifying lens 35, the syringe must be ejected from the syringe cavity for use. Syringe ejection is easily effectuated by sliding the cover 3 toward the syringe cavity 13 end of the base 1. The cover 3 is then slid back toward the vial cavity end of the base 1. This action forces the cover 3 against the hilt 66 of the syringe 60 thereby pushing the syringe 60 out of the syringe cavity 13 and exposing the syringe hilt 66 so that it may be easily grabbed and removed with the user's fingers.

In order to ensure that cover 3 does not unintentionally slip into a position where vial 50 may slip or be knocked out of vial cavity 20, track detents 40 are formed along the track. As cover 3 is slid along track 25 from the position most proximate to vial cavity 20, cover flanges 27 come into physical contact with track detents 40 which act to prevent cover 3 from slipping past a point where vial 50 can be removed from vial cavity 20. Track detents 40 are constructed of elastic material to allow cover 3 to be easily pushed beyond the detent position so that the cover 3 may be positioned to allow for vial removal or syringe ejection when desired. However, track detents 40 provide sufficient resistance to sliding to prevent cover 3 from inadvertently sliding into a position that will allow vial loss or damage. In the preferred embodiment of the present invention track detents 40 are constructed of thin, elastic, arcuate members which deflect to allow cover flanges 27 to pass by when cover 3 is pushed by the user.

Cover 3 may be formed with tabs or flanges to aid the physically impaired in sliding the cover 3 into the various positions required for use, however, these flanges have been omitted in the embodiment shown in the accompanying figures for clarity and compactness of design. Cover tabs or flanges have not been found necessary for most physically impaired users.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed is:

1. A syringe loading aid comprising:
   a base having an ergonomically designed hour-glass shape and exterior texture to facilitate handling and hand-held usage;
   a first base cavity in said base formed to receive a medicine vial, said vial comprising a vial body, vial neck, vial cap, vial label and a septum, said first base cavity having a vial body section shaped to contain and protect at least a portion of a vial body, said first base cavity further comprising a vial neck section shaped to positively lock a vial neck in a releasable interference fit, said first base cavity further comprising a vial cap section shaped to positively lock a vial cap in a releasable interference fit so as to prevent longitudinal movement and inhibit lateral movement of a vial when placed within the first base cavity;
   a second base cavity in said base formed to receive a syringe of the type comprising a needle, a barrel, syringe markings, a hilt and a plunger, said second base cavity being shaped to position said syringe in substantial coaxial alignment with a vial in said first base cavity so that a syringe needle will properly puncture a septum of a vial cap when a syringe is inserted into said second base cavity;
   a protective cover attachable to said base;
   said cover enclosing said first base cavity thereby protecting at least a portion of a vial body and restraining a vial from lateral movement;
   said cover also enclosing said second base cavity thereby preventing a syringe inserted into said second base cavity from lateral movement and protecting a syringe while it is inserted into said second base cavity;
   a syringe clenching device positioned to frictionally contact at least a portion of a syringe when a syringe is inserted into said second base cavity, said frictional contact being sufficient to resist movement of said syringe in a lateral and a longitudinal direction; and
   a needle guide shaped to guide a syringe into substantially coaxial alignment with a medicine vial in said first base cavity by guiding a needle into said second base cavity.

2. The device of claim 1 wherein the cover further comprises one or more magnifying lenses positioned so as to magnify the label on said medicine vial so as to more easily verify that the correct medicine is being dispensed.

3. The device of claim 1 wherein the cover further comprises one or more magnifying lenses positioned so as to magnify the contents of said medicine vial so as to more easily verify the quantity and quality of medicine within the vial.

4. The device of claim 1 further comprising a release mechanism for ejecting a vial from said base by forcing a vial cap and a vial neck out of said releasable interference fit in said first base cavity.

5. The device of claim 1 further comprising one or more mounting elements with which the device may be attached to a wall, table or other surface using fasteners.

6. The device of claim 1 wherein said second base cavity and said cover are shaped to receive a plurality of standard syringe sizes and said clenching device is constructed so as to frictionally resist movement of said plurality of standard syringe sizes.

7. A portable, hand-held syringe loading aid comprising:
   a medicine vial holder for holding a medicine vial of the type having a vial body, vial neck, vial cap, a vial label and a septum, said vial holder being shaped to loosely surround at least a portion of a vial body and to secure by interference fit a vial neck and vial cap so as to protect a vial and prevent vial movement relative to the loading aid;
   a syringe holder for holding a syringe of the type having a needle, a syringe barrel, a syringe hilt, markings, and a syringe plunger, said syringe holder having an entrance by which a syringe may enter the holder, said holder being shaped so as to contain and protect a syringe during hand-held use and transport, to guard a needle from contact with internal surfaces and to align a needle with a septum of a vial so that a needle properly punctures a septum as a syringe is inserted into the syringe holder;
   a syringe clench that frictionally contacts a syringe when it is inserted into the syringe holder so as to resist longitudinal motion of the syringe as a syringe plunger is extracted during loading;
   a syringe needle guide for physically directing a syringe needle into the syringe holder; and
   a push-button vial ejector for releasing a vial from said releasable interference fit.

8. The device of claim 7 wherein said one or more lenses is positioned adjacent the vial so as to magnify the vial.

9. A portable syringe loading device adapted for hand-held use comprising:
   a vial holder for holding a vial containing liquid contents, said holder having an exterior shape that easily fits the hand and exterior surfaces with friction inducing texture to inhibit slippage in the hand said holder also being configured to form an in interference snap fit on a cap of a vial;
   a syringe holder for holding a syringe in relative position to a vial in said vial holder to allow the contents of said vial to be extracted into a syringe having a needle, a body, and a plunger;

a slidable, transparent cover to protect a vial when placed in said vial holder and a syringe when placed in said syringe holder, said cover comprising lenses to magnify a vial and its contents; and a push-button ejection mechanism to release a vial from said interference snap fit in said vial holder.

10. The syringe loading device of claim 9 wherein said syringe holder comprises a clenching device that frictionally holds a syringe in said holder while a syringe plunger is being retracted for syringe filling; and a syringe ejection mechanism to eject a syringe from said clenching device.

11. A readily portable, hand-held syringe loading apparatus comprising:

a base having a tapered, hour-glass shape to facilitate hand-held use and inhibit slippage while being held in a hand, a vial cavity formed in said base, said vial cavity being shaped to partially surround a vial and provide protection for said vial during hand-held use and transport, said vial cavity comprising;
   a vial body section having a substantially semi-circular shape capable of closely receiving a vial body and providing protection therefor;
   a vial neck section having a shape that provides an interference snap fit for a vial neck;
   a vial cap section having a shape that provides an interference snap fit for a vial cap;

a push-button vial release mechanism, integral to said base, for releasing a vial cap from said interference snap fit for a vial cap and releasing a vial neck from said interference snap fit for a vial neck;

a syringe cavity formed in said base, said syringe cavity being in substantial coaxial alignment with said vial cavity, said syringe cavity being connected to said vial cavity and said syringe cavity having a syringe stop such that a syringe inserted into said syringe cavity is prevented from penetrating into said vial cavity, but a needle on a syringe inserted into said syringe cavity will be allowed to penetrate into said vial cavity;

clench tensioners attached to said base, said tensioners configured to allow axial entry of a syringe into said syringe cavity and apply sufficient force on a syringe to prevent unintended extraction during syringe loading;

a transparent cover longitudinally slidably attached to said base, said cover providing protection for a vial placed in said vial cavity and for a syringe placed in said syringe cavity, said cover also providing visual magnification of a syringe in said syringe cavity and a vial in said vial cavity.

12. The apparatus of claim 11 wherein said interference snap fit of said vial neck section and said interference snap fit of said vial cap section are achieved by extending the circular shape of said vial neck section and said vial cap section beyond a half circle for about 0.06 inches.

13. A syringe loading device comprising:

a vial holder adapted to hold a vial containing liquid contents, the vial holder having an integrated interference snap fit to removably receive a cap of the vial;

a syringe insertion guide and holder, adjacent the vial holder and integrated therewith, adapted to allow a syringe having a needle at one end, which is attached to a body with a plunger in a second end, to be removably inserted needle end first into the syringe insertion guide and holder with the needle penetrating into the vial in said vial holder, the syringe insertion guide and holder further comprising biased syringe clamps that hold the body of the syringe in a removably fixed position;

a transparent cover slidably mounted parallel to the vial holder and syringe insertion guide and holder to protect the vial and syringe when placed in said syringe holder, the transparent cover slidable to a first position uncovering the vial holder, to a second position covering the vial holder and allowing insertion of the syringe into the syringe insertion guide and holder, and intermediate the first and second positions to eject the syringe at least partially for removal; and a push-button vial ejector, fitted in the vial holder and adjacent the interference snap fit.

* * * * *